US010930007B2

(12) United States Patent
Kruecker (10) Patent No.: US 10,930,007 B2
(45) Date of Patent: Feb. 23, 2021

(54) SYSTEM AND METHOD FOR MEDICAL DEVICE TRACKING (71) Applicant: KONINKLIJKE PHILIPS N.V., Eindhoven (NL)

(72) Inventor: Jochen Kruecker, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 348 days.

(21) Appl. No.: 15/779,861

(22) PCT Filed: Dec. 13, 2016

(86) PCT No.: PCT/EP2016/080849
§ 371 (c)(1),
(2) Date: May 30, 2018

(87) PCT Pub. No.: WO2017/102761
PCT Pub. Date: Jun. 22, 2017

(65) Prior Publication Data
US 2020/0302636 A1 Sep. 24, 2020

Related U.S. Application Data (60) Provisional application No. 62/266,733, filed on Dec. 14, 2015.

(51) Int. Cl.
G06T 7/73 (2017.01)
G06T 7/246 (2017.01)
A61B 8/00 (2006.01)

(52) U.S. Cl.
CPC .............. G06T 7/73 (2017.01); A61B 8/4254 (2013.01); G06T 7/246 (2017.01)

(58) Field of Classification Search
CPC ..... A61B 8/4254; A61B 5/065; A61B 5/0077; A61B 8/13; G06T 7/73; G06T 7/246; G06T 7/004
See application file for complete search history.

(56) References Cited

U.S. PATENT DOCUMENTS

| 6,122,538 | A | 9/2000 | Sliwa et al. |
| 6,296,613 | B1 | 10/2001 | Emmenegger et al. |
| 6,315,724 | B1 | 11/2001 | Berman et al. |
| 9,135,707 | B2 | 9/2015 | Jain |
| 2006/0241432 | A1 | 10/2006 | Herline et al. |
| 2013/0016185 | A1 | 1/2013 | Stolka et al. |
| 2013/0072787 | A1* | 3/2013 | Wallace ................. A61B 6/461 600/424 |
| 2013/0237811 | A1* | 9/2013 | Mihailescu .......... A61B 8/4438 600/424 |
| 2016/0258782 | A1* | 9/2016 | Sadjadi ................ G01D 18/008 |

FOREIGN PATENT DOCUMENTS

| AU | 2011100156 A4 | 2/2011 |
| CN | 2012001548 A | 5/2013 |

* cited by examiner

Primary Examiner — Leon Viet Q Nguyen (57) ABSTRACT

A system (100) for tracking the position and orientation (i.e., the pose) of a medical imaging device (210) is described. The system determines in real time the pose of an imaging medical device based on a combination of image data and sensor data obtained from an imaging medical device and tracking sensors (210) associated with the device. Pose is determined based on a calculated tracking pose change and a calculated image pose change and a determined reliability of the calculated tracking pose change and the calculated image pose change.

15 Claims, 3 Drawing Sheets

SYSTEM AND METHOD FOR MEDICAL DEVICE TRACKING

CROSS-REFERENCE TO PRIOR APPLICATIONS

This application is the U.S. National Phase application under 35 U.S.C. § 371 of International Application Serial No. PCT/EP2016/080849, filed on Dec. 13, 2016, which claims the benefit of U.S. Patent Application No. 62/266,733, filed on Dec. 14, 2015. This application is hereby incorporated by reference herein.

BACKGROUND

Technical Field

This disclosure relates to tracking an imaging medical device, and more particularly to systems and methods that provide accurate real time determinations of the three dimensional pose of an imaging medical device.

Description of the Related Art

Tracking systems for tracking invasive medical devices that employ optical, electromagnetic or ultrasound tracking systems can be expensive and sometimes may require significant setup time. For example, setting up a field generator for electromagnetic tracking can be very complicated procedure.

Some medical devices such as an ultrasound imaging device do not require a high degree of accuracy with regard to knowing the position and orientation, e.g., the pose, of the device. Still, while some pose information can be derived from the images provided by the device, without more, such devices do not provide a complete determination of the pose of the device.

The high cost of commercially available medical device tracking systems does not justify their use in certain medical procedures. The capabilities of these systems provide accuracy that far exceeds what is acceptable for certain medical procedures, such as a procedure employing an imaging medical device.

SUMMARY

In accordance with the present principles, a system and method for tracking the position and orientation (i.e., the pose) of a medical imaging device is described. The system determines the three-dimensional pose of an imaging device in real-time through the combination of image data and sensor data. The system includes a tracking module configured to generate tracking pose change data of the imaging device obtained from a tracking sensor associated with the imaging device. The system also includes an image tracking module configured to track image pose change data of the imaging device obtained from images generated by the imaging device. A module determines the imaging device current pose based on a combined image device pose change and a previously determined pose of the imaging device. The module determines the combined image device pose change in a computation based on the tracking pose change data, a reliability value determined for the tracking pose change data, the image-based pose change data, and a reliability value determined for the image-based pose change data.

According to present principles, also described is a method for determining the three-dimensional pose of an imaging device in real-time through the combination of image data and sensor data obtained from an imaging medical device and a tracking sensor associated with the device. According to the method, a tracking pose change of an imaging device is determined from information provided by a tracking sensor associated with the imaging device and an image-based pose change of the imaging device is determined from image information provided by the imaging device. The reliability of the tracking pose change and the reliability of the image-based pose change are determined. The combined pose change of the imaging device is determined based on the tracking pose change, the image-based pose change, the determined reliability of the tracking pose change and the determined reliability of the image-based pose change. The current pose of the imaging device is determined from the combined image device pose change and a previously determined pose of the imaging device.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems and methods are provided for determining a combined best pose change estimate of an imaging medical device. Users benefit from the improved pose determination accuracy and achieve higher success rates in performing medical procedures, such as prostate cancer biopsies.

In one embodiment, a system, in accordance with the present principles, uses data obtained in real time from inertial sensors coupled to the device, e.g., micro-electro-mechanical sensors, and image frame data obtained in real time from an imaging medical device, e.g., an ultrasound probe. In another embodiment, a system, in accordance with the present principles, uses data obtained in real time from optical sensors coupled to the device, e.g., infrared sensors, and image frame data obtained in real time from an imaging medical device, e.g., an ultrasound probe. In another embodiment, inertial tracking sensors, optical tracking sensors, and image-based sensors are employed to track the medical device.

The system combines the data from the different tracking sources to determine pose change and to provide the current real time pose. It should be understood that the present principles will be described in terms of medical instruments; however, the present principles are much broader and are applicable to any image based technology that involve pose determination. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk read only memory (CD-ROM), compact disk read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, image, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Figure 1:
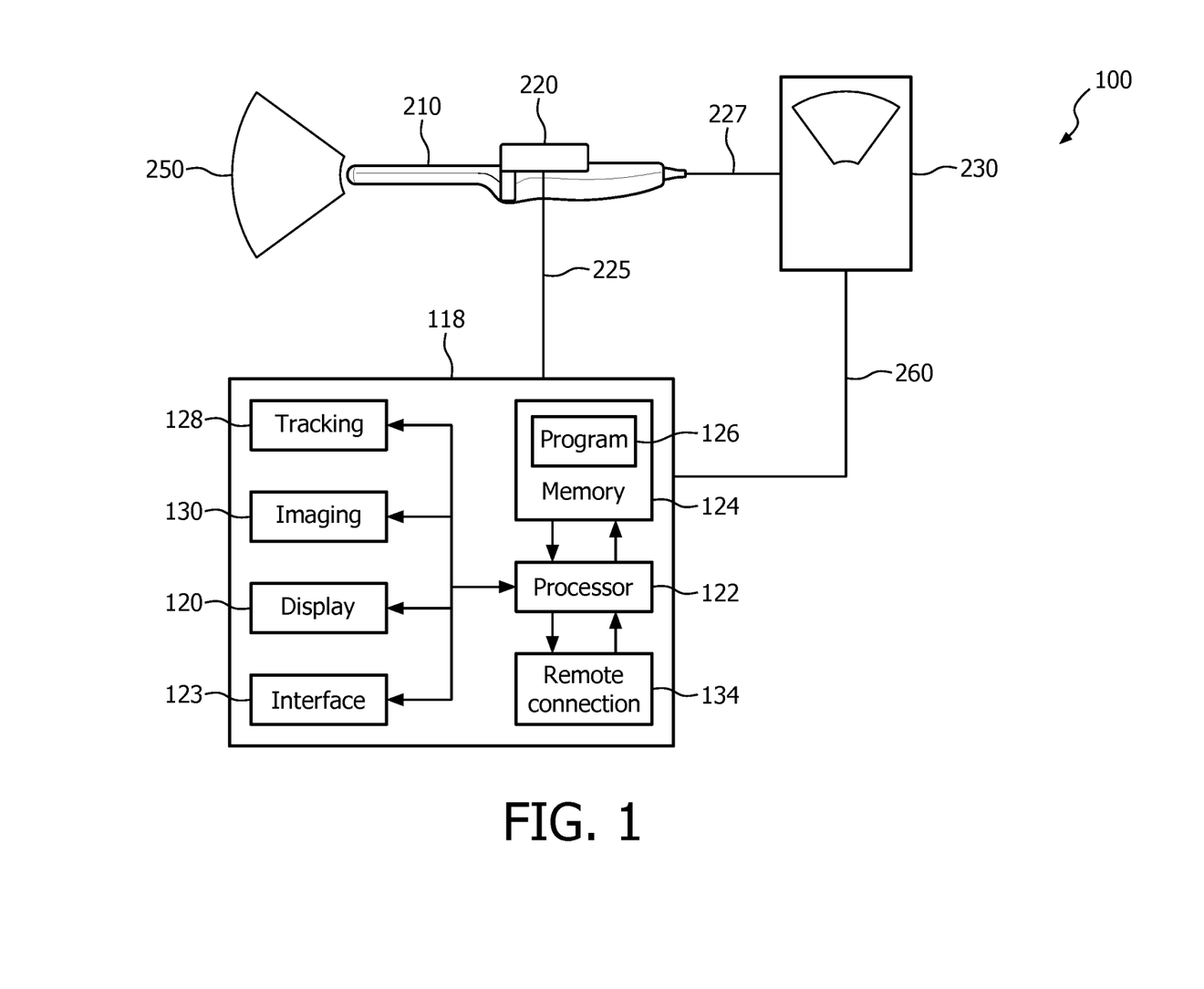
FIG. 1 depicts a system for determining the pose change of an imaging medical device in accordance with present principles.

Referring now to the drawings in which like numerals represent the same or similar elements and initially to FIG. 1, an illustrative system 100 is depicted which employs tracking with an imaging medical device in accordance the present principles. System 100 illustratively depicts an imaging probe 210. For purposes of present principles, the imaging probe 210 is exemplarily represented as an ultrasound probe that generates an ultrasound image plane 250. Imaging probe 210 is coupled to an ultrasound scanner 230 by connector 227. The ultrasound scanner 230 is operatively coupled to workstation 118 by connector 260. Ultrasound scanner 230 generates a series of real-time 2D or 3D ultrasound or other images which may be displayed on the scanner. Through connector 260, the scanner 230 provides a stream of image-based data to the workstation 118.

Probe 210 is shown coupled to an inertial tracking sensor 220, e.g., a micro electromechanical sensor. Inertial tracking sensor 220 is operatively coupled to workstation 118 by connector 225 and provides a stream of tracking data to the workstation 118. A single inertial tracking sensor may be employed, or two or more inertial tracking sensors may be employed. The sensors may be positioned on the imaging probe 210, or they may be embedded within or under a probe surface. Micro electro-mechanical systems (MEMS) exemplify the inertial tracking sensors that can be used according to present principles. MEMS sensors are mass-produced at low cost and are accurate for determining linear acceleration, and have a few degrees per hour bias stability for rotation.

System 100 employs an inertial tracking system 128 for tracking the data provided by the micro electromechanical sensor 220. Other tracking technologies that may be employed include and infrared tracking system. In an optical tracking system, an infrared camera-based computer input device uses a camera to detect signals from an infrared sensor source in order to optically track a medical device.

Figure 2:
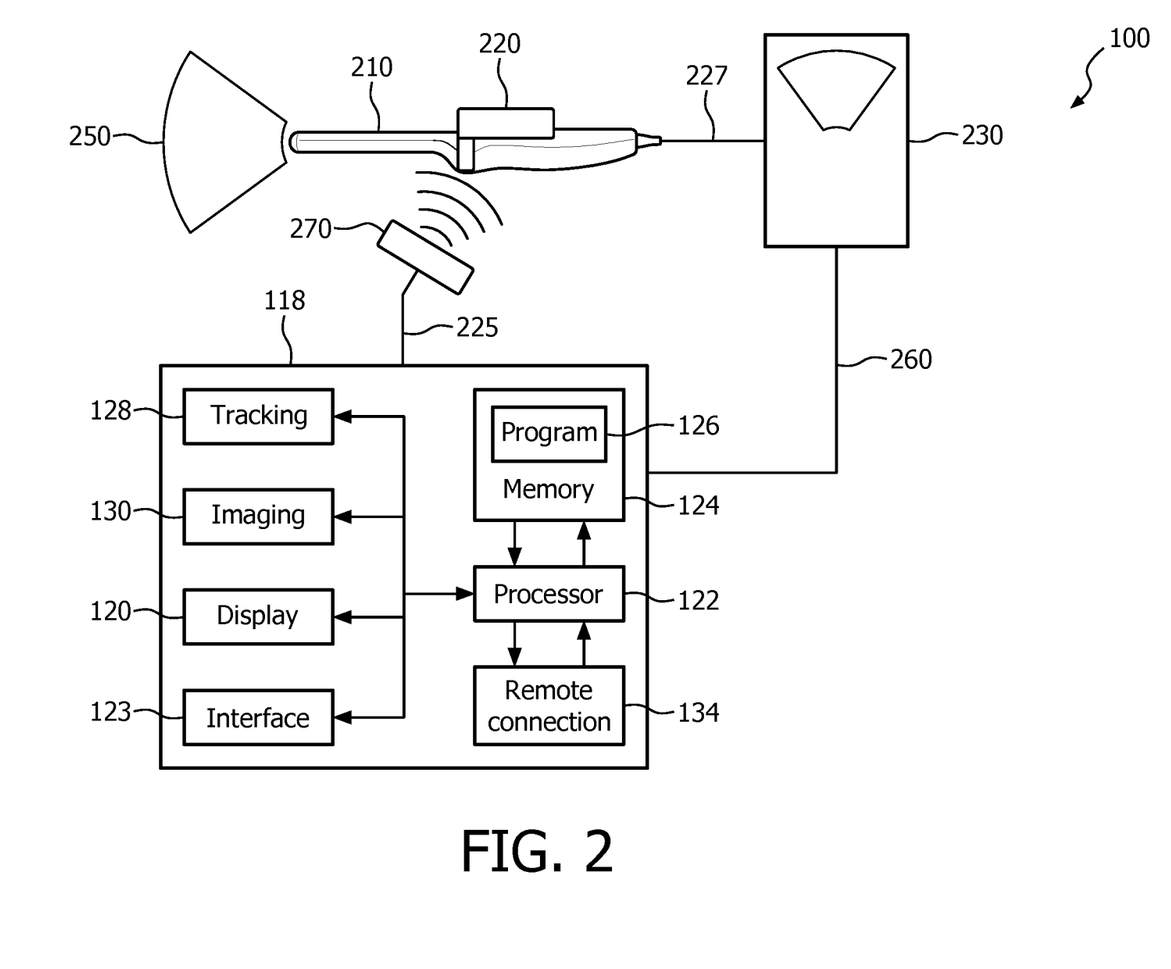
FIG. 2 depicts another system for determining the best pose change of an imaging medical device in accordance with present principles.

Referring to FIG. 2, an infrared-camera tracking device is employed, where camera 270 receives information from tracking sensor 220 that is coupled to the imaging probe 210. Camera 210 is operatively coupled to workstation 118 by connector 225. Components of FIG. 2 are otherwise similar to the components of FIG. 1 and are numbered similarly.

Tracking data is transferred from the tracking system 128 in real-time. The workstation 118 runs software programs (e.g., program module 126) to track devices to provide real time information on the estimated pose of the image probe 210 by combining real time tracking information from the ultrasound images and the inertial sensors and/or the infrared camera sensing system and visualizes the three dimensional pose of the imaging probe on a display 120.

The workstation 118 may include a console from which a procedure is supervised and/or managed. Workstation 118 preferably includes one or more processors 122 and memory 124 for storing programs and applications. An imaging system 130 may be provided and employed during a procedure. Imaging system 130 collects and tracks image data sent by the probe 210 and renders the data on display 120. In one embodiment, the ultrasonic probe 210 may be connected to a stepper (not shown) that is used during a medical procedure to provide controlled motion for advancing and retracting the ultrasonic probe 210. Memory 124 may store programs for controlling the stepper to move a position of the ultrasonic probe 210.

According to present principles, memory 124 includes a program module 126 for processing data relating to the pose of the probe 210 as determined from the tracking frame data obtained from the inertial tracking sensors and as determined from the image frame data obtained from the ultrasound probe 210. The pose change information from these sources can be processed by an imaging device current pose determining module, e.g., one that could be within program module 126, to determine the current pose of the imaging device. The determination of pose is based on a combined determination of the change in pose and previously-known pose of the device. The combined determination of the change in pose is computed in the module from information including: the change in pose determined from the tracking frame data; a reliability score for same that is determined based on one or more reliability parameters; the change in pose as determined from the image frame data; and a reliability score for same that is determined based on one or more reliability parameters. The combined pose change determination, as based on these considerations, is used by the module to determine a current, updated pose, e.g., a pose determination in real time, by updating a recently known pose of the device.

The imaging device current pose determining module 126 may use the three dimensional (3D) pose determination to position the individually acquired two dimensional (2D) ultrasound images in a 3D space, thereby providing an extended field of view, or a 3D representation of the imaged area. The module may also use the 3D pose determination to place 2D ultrasound images in the correct spatial relationship with a pre-acquired 3D image. Examples of 3D images include images generated by computed tomography (CT) and magnetic resonance imaging (MRI)). Systems that fuse or combine ultrasound and CT or MRI include the Philips® UroNav™ (MRI) and the Philips® PercuNav™ (CT) systems. The tracked ultrasound images, with current pose determination of the imaging device are superimposed on or fused with the corresponding part of the CT or MR image, and allow medical personnel with the ability to see the same anatomical region in two different modalities.

Module 126 may be configured to provide workflow instructions for a user through use of an interface 123 and/or display 120 for reviewing process steps, tracking data and archiving data. The module 126, using the display 120 and the user interface 123, prompts and guides the user to follow a specific workflow or may be employed for generating a plan before a procedure is performed. The interface 123 may include a keyboard, mouse, a joystick, a haptic device, or any other peripheral or control to permit user feedback from and interaction with the workstation 118. The system 100 may include a remote connection 134 for remote data transfer to an agent outside the setting where the system 100 is being employed (e.g., the vendor or service contractor of the system 100) or for other uses.

Figure 3:
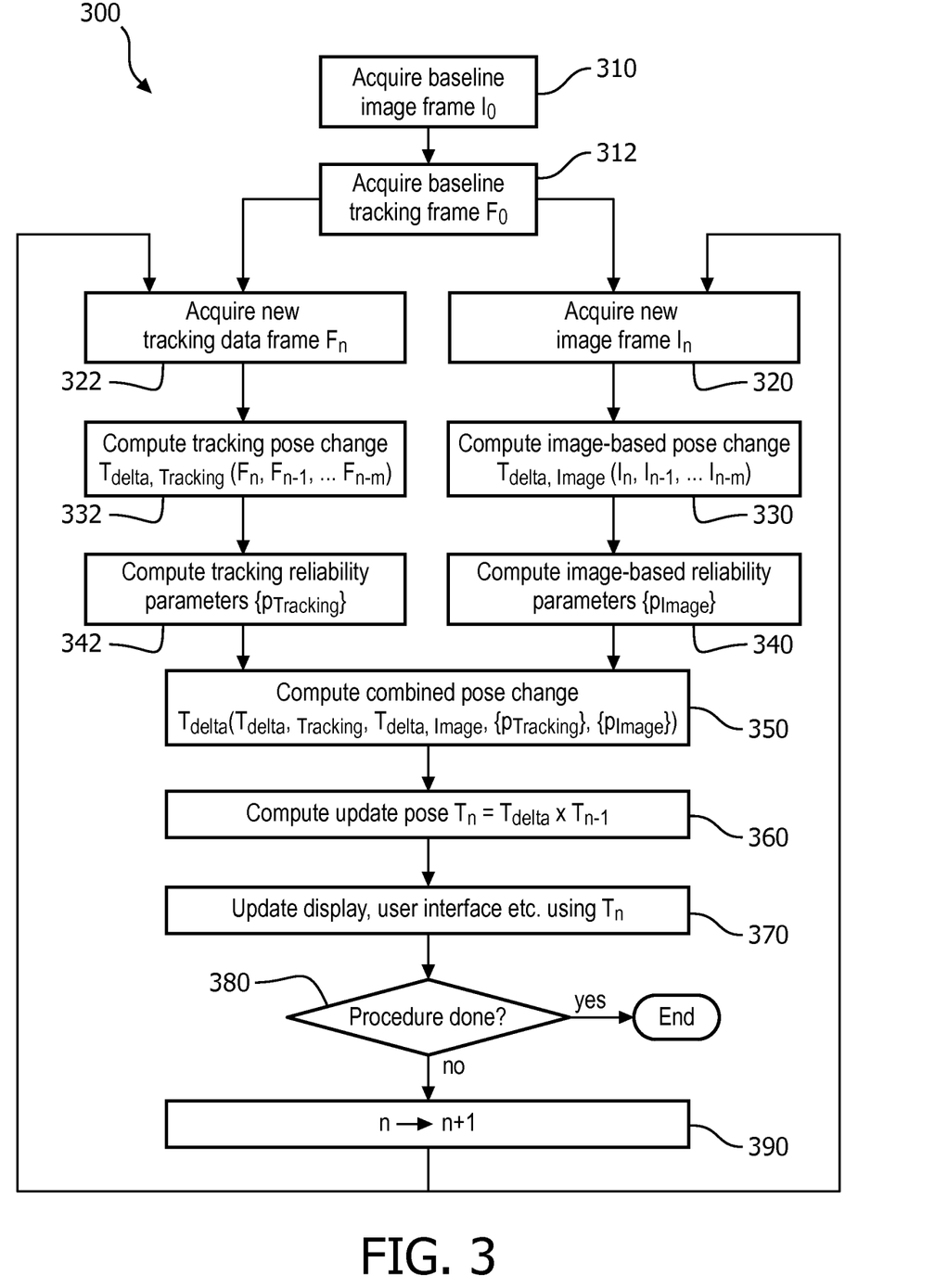
FIG. 3 is a block diagram showing a method for determining the pose change of an imaging medical device in accordance with present principles.

Referring to FIG. 3, a method 300 is illustratively shown for determining the pose of an imaging medical device, e.g., an ultrasound probe, from a combination of two or more kinds of tracking data information in accordance with the present principles. In the described exemplary embodiment, the ultrasound probe has an inertial sensor, e.g., a MEMS sensor, associated with the probe and which provides tracking frame data that is used to determine a tracking-based pose change. The ultrasound probe provides image-based data that is used to determine an image-based pose change. The image-based pose change information and the tracking-based pose change information are combined with information concerning the reliability of the image-based pose change information and the tracking-based pose change information to provide a best real time determination of the pose change of the imaging medical device, which is then used to determine the updated pose of the imaging medical device. Furthermore, the system 100 can perform the activities described below.

In blocks 310, 312, baseline information is obtained, e.g., a baseline image frame $I_0$ (310) and a baseline tracking frame $F_0$ (312) are obtained. These frames could be taken at the beginning of the procedure and could provide the information for determining the initial pose of the ultrasound probe.

New image data frame (320) and a new tracking data frame $F_n$ (322) are obtained in blocks 320 and 322 and reflect the positional change of the probe since the baseline image frame and baseline tracking frame were obtained in blocks 310 and 312.

In blocks 330 and 332, image-based pose change $T_{\Delta, Image}$ (330) and tracking-based pose change $T_{\Delta, Tracking}$ (332) are computed. $T_{\Delta, Image}$ represents the pose difference between a pair of images in sequence (e.g., images $I_n$, $I_{n-1}$) or a number of images in sequence (e.g., images $I_n, I_{n-1}, \ldots I_{n-m}$). In a similar way, $T_{\Delta, Tracking}$ represents the pose difference between a pair of frames in sequence (e.g., frames $F_n, F_{n-1}$) or a number of frames in a sequence (e.g., $F_n, F_{n-1}, \ldots F_{n-m}$). As an example, with a history of two image frames, the image-based pose change estimate between frames $I_{n-2}$ and $I_n$ can be obtained in a relatively direct way as:

$$T_{\Delta,direct}=T_\Delta(I_n,I_{n-2}) \tag{1}$$

or it can be obtained in steps in the following way:

$$T_{\Delta,steps}=T_\Delta(I_n,I_{n-1}) \times T_\Delta(I_{n-1},I_{n-2}) \tag{2}$$

and the combined estimate can be obtained using the averaging of the two methods, i.e.

$$T_{\Delta,combined}=0.5*(T_{\Delta,direct}+T_{\Delta steps}) \tag{3}$$

Further, it should be understood that the tracking frame data and image frame data may be obtained asynchronously with respect to each other. For example, more than one frame of data may be obtained and processed for a given tracking data stream before a frame of the other data stream is obtained.

$I_n$ blocks 340 and 342, image-based reliability parameters $p_{image}$ (340) and tracking reliability parameters $p_{Tracking}$ (342) are computed, in the manner explained below.

In block 350, the combined pose change $T_\Delta$ ($T_{\Delta,\ Tracking}$, $T_{\Delta,\ Image}(p_{Tracking})(p_{image})$) is calculated. An algorithm is employed to calculate the combined pose change, accounting for statistical noise and other inaccuracies to arrive at a best estimate of pose in real time.

In block 360, the updated pose $T_n$ is calculated based on the combined pose change $T_\Delta$ that was calculated. The updated pose change $T_n$ is calculated based on the combined new pose change $T_\Delta$ and the previous pose $T_n-1$, according to $T_n=T_\Delta \times T_{n-1}$.

In block 370, the updated pose change $T_n$, e.g., current pose change, is used to update the display in the user interface, e.g., a display apparatus.

In decision block 380, it is determined if the procedure has been completed. If so, then the method for calculating a combined pose change is terminated. If the procedure is not terminated, then the value of n is increased by 1 (n→n+1) in block 390 and the process returns for another iteration that starts with blocks 320 and 322 with the acquiring of new image $I_n$ frame and new tracking data frame $F_n$, which becomes the basis for the determinations in blocks 330 and 332.

The tracking-based pose-data and the image-based pose data have accuracy limitations that are dependent upon a number of factors, e.g., limitations in the technology, the content of the obtained information (e.g., tracking information, image content), and the manner in which the probe is moved through the patient. As such, the extent to which the tracking-based data and image-based data should be relied on in determining pose change varies with the accuracy of the data. According to present principles, the degree of accuracy is factored into the determination of the reliability of the data provided by the tracking streams.

The reliability of tracking frame data is dependent on one set of quantities that influence data reliability and the reliability of image frame data is dependent on another set of quantities. A given quantity may have a different influence on a given tracking system. For example, while an inertial sensor, e.g., a MEMS sensor, is suited for accurately reporting data pertaining to large accelerations and velocities (high data reliability), large accelerations and velocities could have an adverse effect on image-based data obtained from an imaging probe (low data reliability).

There are up to six (6) degrees of freedom (6-DoF) e.g., three (3) translations (i.e., spatial degrees) and three (3) rotations that a tracking system may detect, and reliability parameters can be defined for tracking the specific degrees of freedom. The reliability parameters can have variable components that are reflective of aspects of probe operations in real time, e.g., position-dependent, velocity-dependent, and acceleration-dependent reliability parameters in each of the three components of translation and the three components of rotation. Various factors affect the accuracy and reliability of the tracking information provided by a tracking system. For example, the reliability of tracking data deriving from an inertial sensor could be effected by the medical device movement. In another example, the reliability of image data deriving from an imaging probe could be affected by probe movement and image quality.

Different tracking sensor systems are affected differently by different factors. The accuracy of movement tracked in one or more of the six (6) components of the 6-DoF could be affected in ways that influence the accuracy and reliability of the tracking data. Other factors, such as accelerations in the movement of the medical device could also affect the accuracy and reliability of the tracking data.

One or more measurable and/or observable quantities that could affect a given tracking system are considered in the reliability determinations. For example, the measurable and/or observable quantities that can affect the reliability of a tracking pose change based on data provided by inertial tracking sensors are acceleration (a), velocity (v), and rotational velocity (w). For an optical sensor, the measurable and/or observable quantities are the distance from camera to optical sensor (d), the correlation between camera image of tracker and the internal model of the tracker (c), and the orientation of the tracker to the camera (o). For ultrasound image-based tracking, in addition to what is said above, quantities include image frame to image frame correlation (cc), mean brightness of the image (m), and the entropy of the image (h), as a measure of information content of the image.

Five (5) degrees of freedom (5-DoF) can be tracked with some low-cost optical tracking systems, which do not track the rotation of the tracking sensor about its axis (e.g., the $6^{th}$ DoF). In a situation where such a low cost 5-DoF optical-based tracking is employed, the tracking-based reliability parameter for the sensor rotation around its axis would be 0, and the entire estimate of that parameter would result from the image-based pose estimate.

In an exemplary embodiment, the reliability parameter for each tracking system can be determined as the product of reliability functions for each of the collected individual measurable and observable quantities. For example, for each tracking system TS, e.g., inertial tracking, optical tracking and image-based tracking, a total reliability parameter $R_{total,\ TS}$ for a tracking system can be determined as:

$$R_{total,TS}=\Pi_{i=1}^{numQuantities}R_{i,TS}(a_i) \qquad (4)$$

Where the $a_i$ are the values of the different quantities considered for a given tracking system TS, e.g., an inertial tracking system, and $R_{i,TS}$ are the individual reliability parameter functions for each of the quantities for the given tracking system TS. For example, the quantities for inertial tracking, as mentioned earlier, are acceleration, velocity, and rotational velocity. In this case, $a_1$ would be the current acceleration, $a_2$ the velocity, and $a_3$ the rotational velocity. $R_1$ then is the reliability as a function of acceleration, $R_2$ the reliability as function of velocity, and $R_3$ the reliability as function of rotational velocity. The total reliability parameter for the tracking system is a product of the individual reliability functions, as indicated by $\Pi_{i=1}^{numQuantities}R_{i,TS}$ in equation (4) above Based on a determination of the reliability of the data obtained from a given tracking system, the quantities considered for a given tracking system are assigned values in the range 0 to 1, with values at or near 1 being assigned when it is determined that the given quantity is in an ideal and/or acceptable range. Conversely, the quantities are assigned a value at or near 0 when it is determined that the quantity is not in an acceptable range because, for example, the quantity deviates from what is reliable. For example, a deviation could occur when tracking conditions for the given tracking system are not ideal, thereby producing data that is of questionable reliability, e.g., the data provided by an inertial tracking system may not be reliable when probe movements are slow or nonexistent. The noisiness of an inertial tracking sensor would adversely influence the tracking frame data in this instance. A $R_{total,TS}$ of 0 would be assigned if all of the measured quantities for a given tracking system deviate from the acceptable range and accordingly the data supplied by the given tracking system technology is not reliable.

In some instances, a particular quantity could affect reliability scores in more than one tracking system. For example, probe velocity (v) may adversely effect on image-based pose data estimate and may thus may be factored into reliability determinations for both inertial and image-based technologies, with different parameters $x_0$ and s for the different tracking systems (as explained below).

The $R_i$ function set forth in equation (1) above can be determined using a Gaussian approach, using a determined ideal value of the quantity, and with a Gaussian width that assigns a 0 value when warranted, e.g., if the quantities for a given tracking system render the data highly unreliable.

In one approach, $$R_i(x) = e^{(-(x-x_0)^2/s^2)} \qquad (5)$$

where x is the determined value of the quantity in question, $x_0$ is the ideal value, and s is a measure of an acceptable range. The values $x_0$ and s can be determined empirically for each particular tracking system, starting with known capabilities and limitations of a given tracking system. Through observation, optimization of what is an ideal value and what is an acceptable rang can be determined.

Empirical determinations of the reliability quantities can be derived from a comparison of the known pose of a probe, as determined by a commercially-available reference tracking technology, to the pose value obtained from a system employing the tracking system combinations described according to the present principles. For example, the NDI Polaris optical tracking system, commercially available from Northern Digital Inc., Waterloo, Calif., could be used as the reference system in the comparison, with pose predictions generated as described above. The values for $x_0$ and s for each quantity pertinent to a given tracking system can be varied within a given range and the pose predictions could be re-determined for one or more iterations in order to arrive at a minimal difference between the reference system pose measurements and the pose measurements as determined by the tracking system combinations described according to the present principles.

The total estimated pose change could be a combined value based on a combination of the pose change estimates that are employed. For example, a combined pose change estimate can be arrived at through a weighted average, the weights given to the individual pose change estimates based on the reliability determinations of the individual tracking systems:

$$T_{\Delta,combined} = \sum_{TS=1}^{numTechnologies} R_{total,TS} * T_{\Delta,TS} / \sum_{TS=1}^{numTechnologies} R_{totalTS} \qquad (6)$$

Where numTechnologies is the number of different technologies employed in tracking (e.g. two (2) if using inertial and image-based tracking and three (3) if using inertial tracking, optical tracking and image-based tracking), $T_{\Delta,TS}$ is the pose (or pose change) estimate obtained from tracking system TS, and $\sum_{TS=1}^{numTechnologies} R_{total,TS}$ is the total sum of the weights, which normalizes the weighted sum of: $R_{total,TS} * T_{\Delta,TS}$.

The calculations for best pose change estimates can be done in accordance to the embodiment described above. In another embodiment, the calculations can be done with a known algorithm such as the Kalman filter. In any event the input data for the "compute combined pose change" step in block 350, i.e., $T_\Delta(T_{\Delta, Tracking}, T_{\Delta, Image}(p_{Tracking})(p_{image}))$ represents the inputs for pose change based on tracking frame data, pose change based on image frame data, the tracking-based reliability parameter and the image-based reliability parameter as described above.

It should be understood that the determinations of estimated pose change, based on tracking frame data, image frame data, and determinations of reliability parameters can be done by the imaging device current pose determining module 126 stored in memory 124 as shown in system 100 of FIGS. 1 and 2.

In another embodiment, the tracking and image-based pose estimates depend not just on the last available data, but on the history of recent data points (indicated by the index m in FIG. 3, where e.g. the image-based estimate for image $I_n$ depends on images $I_n, I_{n-1}, \ldots I_{n-m}+$, with m>=1). One particular way to incorporate the frame history is to obtain estimates for multiple combinations of image frames within the history, and average the results.

In accordance with the present principles, the systems and methods described herein provide an accurate determination of the three-dimensional pose of a medical device in real time. Such a determination can be made for an ultrasound probe employed in a biopsy procedure in which the real time ultrasound images can be combined or fused with MRIs or other reference images. The three dimensional (3D) pose tracking can be used to position the individually acquired two dimensional (2D) images in 3D space, thereby providing an extended field of view, or a 3D representation of the imaged area. The 3D pose could also be used to place 2D ultrasound images in the correct spatial relationship with a pre-acquired 3D image (e.g. computed tomography (CT) and magnetic resonance imaging (MRI), such as in the Philips® UroNav™ or PercuNav™ systems). The tracked ultrasound images can superimposed on or fused with the corresponding part of the CT or MR image, providing medical personnel with the ability to see the same anatomical region in two different modalities. For example, the UroNav™ system is an ultrasound-magnetic resonance imaging (MRI) fusion biopsy system used in fused-image guided prostate cancer biopsies. The UroNav™ system fuses magnetic resonance images (MRIs) with transrectal ultrasound (TRUS) images taken in real time. Suspicious tissue sites, e.g., possible prostate cancer lesions, are identified on the fused images by a radiologist. The suspicious sites are target biopsy sites for taking tissue samples. The 3D pose determined in accordance with present principles could be used to place 2D ultrasound images in correct spatial relationship with a pre-acquired 3D MRI image.

One of the advantages of the system in accordance with present principles is that it is provides highly accurate results while still being relatively inexpensive. Little to no setup time is required for the system. A complex component such as a field generator does not have to be used. For example, optical sensors such as infrared sensors are lightweight, small and have a small field of view, an advantageous combination of characteristics because, for example, the camera reader can be positioned close to the imaging device that is being used. This makes it relatively easy to position the camera so it has an uninterrupted line-of-site to the ultrasound probe.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;

d) several "means" may be represented by the same item or hardware or software implemented structure or function; and e) no specific sequence of acts is intended to be required unless specifically indicated.

Having described preferred embodiments for a system and method for medical device tracking (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for determining a three-dimensional pose of an imaging device in real-time through a combination of image data and sensor data, the system comprising one or more processors configured to:
   generate tracking pose change data of the imaging device obtained from a tracking sensor associated with the imaging device;
   track image pose change data of the imaging device obtained from images generated by the imaging device; and
   compute a combined imaging device pose change and to determine a current pose of the imaging device based on the computed combined imaging device pose change and a previously determined pose of the imaging device, wherein the combined imaging device pose change is computed using the tracking pose change data, a reliability value determined for the tracking pose change data, the image pose change data, and a reliability value determined for the image pose change data.

2. The system of claim 1, wherein the one or more processors are further configured to:
   determine the tracking pose change data based on a comparison of relatively newer tracking pose change data and relatively older tracking pose change data.

3. The system of claim 1, wherein the one or more processors are further configured to:
   determine the image pose change data based on a comparison of relatively newer image pose change data and relatively older image pose change data.

4. The system of claim 1, wherein the one or more processors are further configured to:
   determine the reliability value of the tracking pose change data; and
   determine the reliability value of the image pose change data based on one or more factors selected from device acceleration, device velocity, device rotational velocity, distance from a camera to an optical sensor, correlation between camera image of a tracker and internal modeling of the tracker, orientation of the tracker to the camera, correlation of image frame to image frame, mean brightness of the images, and entropy of the images as a measure of image information content.

5. The system according to claim 1, wherein the one or more processors are further configured to position with the current pose of the imaging device, two dimensional images in a three dimensional space.

6. The system according to claim 1, wherein the one or more processors are further configured to position with the current pose of the imaging device, two dimensional images in spatial relationship with a pre-acquired three dimensional image.

7. The system according to claim 1, wherein the tracking sensor is an electromechanical sensor and the imaging device is an ultrasound probe.

8. The system according to claim 1, wherein the tracking sensor is an infrared sensor and the imaging device is an ultrasound probe.

9. A system for determining a three-dimensional pose of an imaging device in real-time through a combination of image data and sensor data, the system comprising one or more processors configured to:
   generate tracking pose change data of the imaging device obtained from a tracking sensor associated with the imaging device;
   track image pose change data of the imaging device through images generated by the imaging device;
   compute a combined imaging device pose change and to determine a current pose of the imaging device based on the computed combined imaging device pose change and a previously determined pose of the imaging device, wherein the combined imaging device pose change is computed using the tracking pose change data, a reliability value determined for the tracking pose change data, the image pose change data, and a reliability value determined for the image pose change data; and
   display images supplied from the imaging device.

10. The system of claim 9, wherein the one or more processors are further configured to:
    determine the tracking pose change data based on a comparison of relatively newer tracking pose change data and relatively older tracking pose change data; and
    determine the image pose change data based on a comparison of relatively newer image pose change data and relatively older image pose change data.

11. A method for determining a three-dimensional pose of an imaging device in real-time through a combination of at least image data and sensor data, the method comprising:
    determining a tracking pose change of the imaging device from information provided by a tracking sensor associated with the imaging device;
    determining an image pose change of the imaging device from image information provided by the imaging device;
    determining a reliability parameter of the tracking pose change and a reliability parameter of the image pose change;
    computing a combined pose change of the imaging device using the tracking pose change, the image pose change, the reliability parameter of the tracking pose change and the reliability parameter of the image pose change; and
    determining a current pose of the imaging device based on the combined pose change of the imaging device and a previously determined pose of the imaging device.

12. The method of claim 11, wherein the determining of the tracking pose change comprises comparing relatively newer data obtained from the tracking sensor and relatively older data obtained from the tracking sensor, and
    the determining of the image pose change comprises comparing relatively newer data obtained from the image information and relatively older data obtained from the image information.

13. The method of claim 11, wherein the determining of the tracking pose change comprises comparing a new tracking frame and one or more older tracking frames obtained from the tracking sensor, and the determining of the image pose change comprises comparing a new image frame and one or more older image frames obtained from the image information.

14. The method of claim 11, wherein the determining of the reliability parameter of the tracking pose change and the determining of the reliability parameter of the image pose change further comprises evaluating one or more factors of a set of factors that influence reliability of the determined tracking pose change and the determined image pose change.

15. The method of claim 11, wherein the tracking sensor is one or more of an inertial sensor and an infrared sensor, and the imaging device is an ultrasound probe.

* * * * *